United States Patent
Buckley

(10) Patent No.: US 7,304,038 B2
(45) Date of Patent: Dec. 4, 2007

(54) THERAPEUTIC COMPOSITION AND METHOD OF SUPPORTING THE IMMUNE SYSTEM

(76) Inventor: Julie A. Buckley, 5270 Palm Valley Rd., Ponte Vedra Beach, FL (US) 32082

( * ) Notice: Subject to any disclaimer, the term of this patent is extended or adjusted under 35 U.S.C. 154(b) by 0 days.

(21) Appl. No.: 11/223,533

(22) Filed: Sep. 9, 2005

(65) Prior Publication Data

US 2007/0059383 A1    Mar. 15, 2007

(51) Int. Cl.
*A61K 38/00*    (2006.01)
*A61K 31/35*    (2006.01)
*A61K 31/34*    (2006.01)
*A61K 31/07*    (2006.01)
*A61K 33/32*    (2006.01)

(52) U.S. Cl. .................. 514/18; 514/458; 514/474; 514/725; 424/641; 424/643; 424/702

(58) Field of Classification Search .............. None
See application file for complete search history.

(56) References Cited

U.S. PATENT DOCUMENTS

| | | | | |
|---|---|---|---|---|
| 5,488,039 | A * | 1/1996 | Masor et al. | .................. 514/43 |
| 5,562,910 | A * | 10/1996 | Daynes et al. | ........... 424/278.1 |
| 5,785,978 | A * | 7/1998 | Porter et al. | ................. 424/401 |
| 5,875,798 | A * | 3/1999 | Petrus | ......................... 132/321 |
| 5,948,443 | A * | 9/1999 | Riley et al. | .................. 424/643 |
| 6,090,414 | A * | 7/2000 | Passwater et al. | .......... 424/702 |
| 6,469,024 | B2 * | 10/2002 | Li et al. | ..................... 514/307 |

* cited by examiner

*Primary Examiner*—Raymond J. Henley, III
(74) *Attorney, Agent, or Firm*—Thomas C. Saitta

(57) ABSTRACT

Disclosed is a therapeutic nutritional compound for treating and supporting the immune response in a mammal, particularly a human baby or child, and the treatment method. Additionally, the therapeutic nutritional compound can be used in conjunction with a vaccine or immunization regimen to reduce the potential undesirable effects caused by other components of the vaccine. The therapeutic nutritional compound can include glutathione, selenium, zinc and antioxidants.

15 Claims, No Drawings

THERAPEUTIC COMPOSITION AND METHOD OF SUPPORTING THE IMMUNE SYSTEM

TECHNICAL FIELD

The present invention relates to a therapeutic composition and in greater detail it relates to a nutritional compound for beneficially supporting the immune function of a mammal, and in particular for the human immune system in the event of stressors such as immunization or illness.

BACKGROUND

There has been a rise in the incidence of Autistic Spectrum Disorder (ASD) since the mid 1980s. This increase cannot be attributed or explained by genetic factors alone. Thus, some have concluded that there is an environmental cause or factor to such disorders. One such factor under suspicion is metal toxicity and especially mercury. Apparently, some children are genetically predisposed to excessive vulnerability and toxicity to mercury. Cumulative exposures from maternal amalgams, Rho D shots for Rh incompatibility, seafood, and especially metal-containing vaccinations take them beyond their tolerance point and into neurotoxic, neurobiologic, neuroimmune and neurometabolic consequence manifesting, to variable degrees as abnormal behaviors, abnormal immune function, abnormal gut function. Fully 60% of autistic children have mothers who are Rh negative (whereas only 8% of women in the general population are Rh negative), and who received the heavily mercury laden Rhogam shots during pregnancy.

Additionally, autistic patients are thought to have defective metallothionein (MT) proteins which normally regulate copper, zinc, heavy metals, gluten and casein digestion, and neuronal development. Elevated copper/zinc ratios are characteristic of ASD, but recently it has also become possible to measure MT proteins in red blood cells directly. Clinical reports already suggest that many autistic children test low on MT protein, and classic features of autism can indeed result from a genetically weakened MT system. Gastrointestinal dysfunction from metal toxicity may prevent these patients from breaking down dietary protein into required amino acids needed for MT protein synthesis, and from maintaining normal intestinal flora. Since MT is directly involved in the neuronal maturation of the brain, the timing of any environmental insults is critically important, and calls attention once again to the vaccination, as well as maternal mercury exposure and amalgam issues.

ASD is thought to be in part a disease of heavy metal induced oxidative stress with predisposing/permissive factors being the vulnerable MT system, vulnerability of the transmethylation and transsulfuration metabolic pathways, by which glutathione, and cysteine, two of the principal detoxifying substances found in the body are synthesized, and the presence of higher levels of testosterone in male children. Testosterone seems to potentiate the adverse effect of MT weakness on the brain, and appears to be partly responsible for slower synthesis of glutathione in males. These effects may account for the 4 to 1 ratio of males to females diagnosed with ASD. When environmental insults such as mercury exposure, whether from vaccines, maternal exposure or diet occur, brain maturation and myelination may be compromised. The theory is that ASD patients do not have so much a damaged brain, but rather one that has not completely matured.

Thus, what is needed is a therapeutic treatment directed to removing ongoing environmental sources of heavy metals, chelating out existing tissue stores of heavy metals, supporting liver detoxification, preloading with zinc and augmenting nutrients, and then gradual introduction of MT and glutathione promoting nutrients. A treatment involving the process of detoxification of the central nervous system, and nutritional support for a weak MT protein and antioxidant buffering system is needed.

The present invention comprises a therapeutic nutritional compound for reducing oxidative stress and supporting immune system function in a mammal, particularly a human baby or child. Additionally, the therapeutic nutritional compound can be used in conjunction with an immunization or vaccine regimen to reduce the undesirable effects caused by the metals in the vaccine. The therapeutic nutritional compound can include glutathione, selenium, zinc and antioxidants.

In greater detail, the therapeutic nutritional compound consists essentially of, on a weight percent basis of the following combined components, from about 20% to about 35% glutathione, less than 1% selenium and from about 60% to about 90% of one or more antioxidant vitamins. In a more preferred embodiment, the compound consists essentially of from about 65% to 75% of one or more antioxidant vitamins. The compound may further include zinc in an amount less than 1%. N-acetyl-cysteine may also be included in amount from 5% to 10%.

The antioxidant vitamins included in the compound may include vitamin A, vitamin E, vitamin C and combinations thereof. Typically, the antioxidant vitamins comprises, by weight of the combined components, from about 20% to about 35% vitamin A, from about 2% to about 7% vitamin E, and from about 35% to about 50% vitamin C.

In a further embodiment, a method of supporting the immune response of a mammal is provided. The method includes administering a therapeutic dose of a compound comprising on a weight percent basis of the combined following components from about 20% to about 35% glutathione, less than 1% selenium, from zero to less than 1% zinc and from about 60% to about 80% of an antioxidant vitamin or combination of antioxidant vitamins. Typically, the dose is between about 300 mg to about 500 mg, and preferably from about 350 mg to about 450 mg, and is administered to a human infant. In dosing, about 1 dose is administered per day to an infant less than 6 months in age, about 2 doses are administered per day to an infant between about 6 months to 12 months in age, about 3 doses are administered per day to an infant between about 12 months to 36 months in age and about 4 to about 5 doses are administered per day to an infant between about 36 months to 60 months in age.

An additional embodiment includes a method of treating a mammal to increase an immune response in vaccination/immunization. The method includes administering a therapeutic dose of a compound comprising, on a weight percent basis of the combined following components, from about 20% to about 35% glutathione, less than 1% selenium, from zero to less than 1% zinc and from about 60% to about 80% of one or more antioxidant vitamins at least once before vaccination and at least once after being vaccinated. The mammal is administered a dose 1-7 days before vaccination, on the day of vaccination and 1-7 days after vaccination. The dose is typically administered to a human infant and/or young child.

DETAILED DESCRIPTION

The present invention comprises a therapeutic nutritional compound that includes on a weight percent basis of the following combined components, from about 20% to about 35% glutathione, less than 1% selenium and from about 60% to about 80% of an antioxidant vitamin. The compound may further include zinc in an amount less than 1%.

The therapeutic nutritional compound can be administered as part of a method for supporting the immune system of mammal in anticipation of vaccination/immunization. Various diseases and syndromes have been associated with vaccinations and it is believed that the present therapeutic nutritional compound and method of administering such greatly reduce the incidences of such consequences.

The ingredients of the therapeutic nutritional compound are listed and claimed on a weight percentage of the combined claimed ingredients only. It is anticipated that other ingredients may be added to the compound mix such as fillers, emulsions and other components that are not to be included in the claimed percentages. The claimed percentages are only listed relative to claimed ingredients.

As used in this application, the term "treat" refers to either preventing, or reducing the incidence of, the undesired occurrence. For example, to treat immune suppression refers to either preventing the occurrence of this suppression or reducing the amount of such suppression. The terms "patient" and "individual" are being used interchangeably and both refer to an animal. The term "animal" as used in this application refers to any warm-blooded mammal including, but not limited to, dogs, humans, monkeys, and apes. As used in the application the term "about" refers to an amount varying from the stated range or number by a reasonable amount depending upon the context of use. Any numerical number or range specified in the specification should be considered to be modified by the term about.

"Dose" and "serving" are used interchangeably and refer to the amount of the nutritional or pharmaceutical composition ingested by the patient in a single setting and designed to deliver effective amounts of the compound. As will be readily apparent to those skilled in the art, a single dose or serving of the liquid nutritional powder should supply the amount discussed in the above in the Summary. The amount of the dose or serving should be a volume that a typical infant between 0 to 6 months can consume in one sitting. This amount can vary widely depending upon the age, weight, sex or medical condition of the patient. However as a general guideline, a single serving or dose of the compound nutritional product should be considered as encompassing a volume of 1-2 teaspoons adding water and sweetener of choice.

Glutathione

Glutathione is a tripeptide and a major reducing agent in the mammalian body. Its chemical structure is GLU-CYS-GLY and its chemical name is glutamyl-cysteinyl-glycine. Like many other small peptides in the mammalian body, it is not synthesized by procedures involving DNA, RNA and ribosomes. Rather, it is synthesized from the amino acids available in the body by procedures utilizing enzymes and other body components such as adenosine triphosphate as an energy source. The glutathione used in the present compound is in a reduced form.

Glutathione may be included in the compound in an amount between about 20% to about 35% and in a further embodiment in an amount between about 25% and 30% and in an additional embodiment in amount of about 27%. As an example, the composition of the compound dose may include between about 50 mg and 150 mg of glutathione and in a further embodiment between about 75 mg and 125 mg and in an additional embodiment about 100 mg.

Selenium

Selenium is one of numerous trace metals found in many foods. In the compositions of this invention, selenium may be employed as one of several non-toxic, water soluble organic or inorganic selenium compounds. Inorganic selenium compounds include aliphatic metal salts containing selenium in the form of selenite or selenate anions, however organic selenium compounds are normally less toxic than inorganic compounds. Other selenium compounds which may be mentioned by way of example include selenium cystine, selenium methionine, mono- and di-seleno carboxylic acids with about seven to eleven carbon atoms in the chain. Seleno Amino acid chelates are also useful. Any of these selenium compounds may be considered for use in the present invention as selenium precursors.

It will be understood, however, that the particular forms of selenium compounds set forth herein are not to be considered limitative. Other selenium compounds, which exhibit the desired activity and are compatible with the other components in the mixture and are non-toxic, can be used in the practice of the invention. Many of them are available commercially.

Selenium may be included in the compound in amount less than 1%. In a further embodiment selenium may be included in amounts less than 0.1%. In an additional embodiment, selenium may be included in amounts less than 0.01%. As an example, the composition of the compound dose may include between 10 and 50 micrograms for selenium and in a further embodiment between 20 and 40 micrograms and in an additional embodiment 30 micrograms.

Antioxidant Vitamins

The antioxidant vitamins for use in the present compound include vitamins A, C and E. The antioxidant vitamin comprises, by weight of the combined components, from about 20% to about 30% vitamin A, from about 2% to about 7% vitamin E, and from about 35% to about 50% vitamin C. In a further embodiment, the antioxidant vitamin comprises, by weight of the combined components, about 27% vitamin A, about 5% vitamin E, and about 40% vitamin C.

As an example, the composition of the compound dose may include between 100 mg to 250 mg of vitamin C, 10 mg and 30 mg of vitamin E and 50 mg and 150 mg of vitamin A. In a further example, the compound dose may include 150 mg of vitamin C, 20 mg of vitamin E and 100 mg of vitamin A.

The term "vitamin E" means a group of tocopherols that have the designations: alpha.-, beta.-, delta.- and gamma.-, that differ only in the number and position of methyl groups on the ring. The most active form of vitamin E, .alpha.-tocopherol, is also the most widely distributed in nature. When .alpha.-tocopherol was first synthesized, the synthetic material was found to have a slightly lower biological activity than the alpha.-tocopherol from plants. Because of this phenomena, the natural occurring form has been designated RRR-.alpha.-tocopherol. For dietary purposes, vitamin E activity is expressed as RRR-.alpha.-tocopherol equivalents (-TEs). One .alpha.-TE is the activity of 1 mg of RRR-.alpha.-tocopherol. One mg of RRR-.alpha.-tocopherol is equivalent to 1.49 IU of vitamin E. The NAS-NRC RDA has been established at 10 mg-TE per day for adult males. Analyses of balanced diets indicate that the average daily intakes of .alpha.-TE range from 7 to 11 mg. Adults tolerate oral doses of 100 to 800 mg/day without symptoms or biochemical evidence of toxicity.

The term "vitamin C" means ascorbic acid. Ascorbic acid intake for adult males between the ages of 20 and 29 years was found to average 121 mg per day (U.S. Dept. of Health and Human Services, 1994). The NAS-NRC RDA for ascorbic acid has been set at 60 mg for adult males. Many people habitually ingest 1000 mg per day of ascorbic acid without developing apparent toxic manifestations.

The term "vitamin A" is used to include retinol and other chemically similar compounds referred to as retinoids. Beta-carotene and other carotenoids are provitamins and are only turned into retinol as the body requires.

Zinc

Zinc is an essential part of more than 100 enzymes involved in digestion, metabolism, reproduction and wound healing. The RDA for zinc is approximately 15 mg. A 200 mg dosage of zinc per day, although well tolerated, has been shown to have potential side effects such as anemia. The anemia associated with high dosage zinc intake is attributable to copper deficiency. Zinc is preferred in the form of an acetate. The zinc component may also be an oxide, which is well tolerated in the digestive system. However, other forms of zinc such as for example zinc gluconate may alternatively be used or be used in combination with zinc acetate in the subject composition.

Accordingly, zinc represents approximately less than 1 percent, in a further embodiment between about 0.2 to 0.9 percent, and an additional embodiment at about 0.7 percent by weight of each dose of the claimed ingredients. As an example, the composition of the compound dose may include between about 1.5 mg and 3.5 mg of zinc and in a further embodiment between about 2.0 mg and 3.0 mg of zinc and in an additional embodiment about 2.5 mg of zinc.

The present inventive subject further matter contemplates the use of biologically-acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders well known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

The plasticizers may be selected from the group consisting of diethyl phthalate, diethyl sebacate, triethyl citrate, cronotic acid, propylene glycol, butyl phthalate, dibutyl sebacate, caster oil and mixtures thereof, without limitation. As is evident, the plasticizers may be hydrophobic as well as hydrophilic in nature. Water-insoluble hydrophobic substances, such as diethyl phthalate, diethyl sebacate and caster oil are used to delay the release of water-soluble vitamins, such as vitamin C. In contrast, hydrophilic plasticizers are used when water-insoluble vitamins are employed which aid in dissolving the encapsulated film, making channels in the surface, which aid in nutritional composition release.

Method

An additional embodiment includes a method of treating a mammal to support an immune response in vaccination. The method includes administering a therapeutic dose of a compound comprising, on a weight percent basis of the combined following components, from about 20% to about 35% glutathione, less than 1% selenium, from zero to less than 1% zinc and from about 60% to about 80% of one or more antioxidant vitamins at least once before vaccination and at least once after being vaccinated. The mammal is preferably administered a dose 2 days before vaccination, on the day of vaccination and 3 days after vaccination. The dose is typically administered to a human infant or child.

Typically, the dose is between about 300 mg to about 500 mg of the claimed ingredients and is administered to a human infant or child. More preferably the dose is between about 350 mg to about 400 mg. In a further embodiment the dose is about 375 mg of the claimed ingredients. In dosing, about 1 dose is administered per day to an infant less than 6 months in age, about 2 doses are administered per day to an infant between about 6 months to 12 months in age, about 3 doses are administered per day to an infant between about 12 months to 36 months in age and about 4 to about 5 doses are administered per day to an infant between about 36 months to 60 months in age. The pre-vaccination doses are administered 1-7 days before vaccination, at least one dose is administered on the day of vaccination and the post-vaccination doses are administered 1-7 days after vaccination.

While there is described herein certain specific embodiments of the present invention, it will be manifest to those skilled in the art that various modifications may be made without departing from the spirit and scope of the underlying inventive concept and that the same is not limited to the particular forms herein described except insofar as indicated by the scope of the appended claims.

What is claimed is:

1. A method of reducing undesirable effects resulting from the presence of metals in a vaccine administered to an infant, comprising the steps of:
   administering to an infant at least one therapeutic dose of a compound consisting essentially of the following components, on a weight percent basis by weight of the combined components:
   from about 20% to about 35% glutathione,
   less than 1% selenium,
   from 0% to less than 1% zinc and
   from about 60% to about 80% of one or more antioxidant vitamins; and
   administering to the infant a vaccine containing metals.

2. The method of claim 1, wherein the therapeutic dose is between about 300 mg to about 500 mg.

3. The method of claim 1, wherein the therapeutic dose is between about 350 mg to about 400 mg.

4. The method of claim 1, wherein the number of doses administered per day to the infant is determined by the age of the infant.

5. The method of claim 4, wherein about 1 dose is administered per day to the infant for an infant less than 6 months in age.

6. The method of claim 4, wherein about 2 doses are administered per day to the infant for an infant between about 6 months to 12 months in age.

7. The method of claim 4, wherein about 3 doses are administered per day to the infant for an infant between about 12 months to 36 months in age.

8. The method of claim 4, wherein about 4 to about 5 doses are administered per day to the infant for an infant between about 36 months to 60 months in age.

9. A method of reducing undesirable effects resulting from the presence of metals in a vaccine administered to an infant, comprising the steps of:
   (a) administering to the infant at least one day prior to vaccination at least one pre-vaccination therapeutic dose of a compound consisting essentially of the following components, on a weight percent basis by weight of the combined components:
   from about 20% to about 35% glutathione,
   less than 1% selenium,
   from 0% to less than 1% zinc and
   from about 60% to about 80% of one or more antioxidant vitamins;
   (b) vaccinating the infant with a vaccine containing metals;
   (c) administering to the infant on the day of vaccination at least one therapeutic dose of a compound consisting essentially of the following components, on a weight percent basis by weight of the combined components:
   from about 20% to about 35% glutathione,
   less than 1% selenium,
   from 0% to less than 1% zinc and
   from about 60% to about 80% of one or more antioxidant vitamins; and
   (d) administering to the infant at least one day subsequent to vaccination at least one post-vaccination therapeutic dose of a compound consisting essentially of the following components, on a weight percent basis by weight of the combined components:
   from about 20% to about 35% glutathione,
   less than 1% selenium,
   from 0% to less than 1% zinc and
   from about 60% to about 80% of one or more antioxidant vitamins.

10. The method of claim 9, wherein said pre-vaccination dose is administered up to seven days before vaccination and said post-vaccination dose is administered up to seven days after vaccination.

11. The method of claim 9, wherein the number of doses administered per day to the infant is determined by the age of the infant.

12. The method of claim 11, wherein about 1 dose is administered per day to the infant for an infant less than 6 months in age.

13. The method of claim 11, wherein about 2 doses are administered per day to the infant for an infant between about 6 months to 12 months in age.

14. The method of claim 11, wherein one or more doses are administered per day to the infant for an infant between about 12 months to 36 months in age.

15. The method of claim 11, wherein about 4 to about 5 doses are administered per day to the infant for an infant between about 36 months to 60 months in age.

* * * * *